United States Patent [19]

Siedle

[11] Patent Number: 4,500,569
[45] Date of Patent: Feb. 19, 1985

[54] PALLADIUM (II) BIS (HEXAFLUOROACETYLACETONATE), ADDUCTS DERIVED THEREFROM AND USES THEREOF

[75] Inventor: Allen R. Siedle, Lake Elmo, Minn.

[73] Assignee: Minnesota Mining and Manufacturing Company, St. Paul, Minn.

[21] Appl. No.: 509,956

[22] Filed: Jun. 30, 1983

Related U.S. Application Data

[62] Division of Ser. No. 351,505, Feb. 23, 1982, Pat. No. 4,410,569, which is a division of Ser. No. 159,367, Jun. 13, 1980, Pat. No. 4,424,352.

[51] Int. Cl.³ .............................................. B05D 3/04
[52] U.S. Cl. .................................... 427/304; 502/334; 502/325; 502/245
[58] Field of Search ...................... 427/304, 437, 215; 252/272; 502/334, 325, 245; 423/579, 437

[56] References Cited

U.S. PATENT DOCUMENTS

| | | | |
|---|---|---|---|
| 3,318,891 | 5/1967 | Hausman | 260/270 |
| 3,356,527 | 12/1967 | Moshier et al. | 117/107.2 |
| 3,538,002 | 11/1970 | Wilson | 252/75 |
| 3,770,785 | 11/1973 | Trofimenko | 260/429 R |
| 3,876,675 | 4/1975 | Trofimenko | 260/429 J |
| 3,883,570 | 5/1975 | Trofimenko | 260/429 R |
| 3,946,057 | 3/1976 | Reedy | 260/439 R |
| 4,042,603 | 8/1977 | Itatani et al. | 260/346.71 |

OTHER PUBLICATIONS

Sievers and Sadlowski, "Volatile Metal Complexes", Science 201, 217–223, (1978).
Okey, Onuki, Nakamura and Kawaguchi, Chem. Lett., 1305, (1977).
Okey, Nakamura and Kawaguchi, J. Chem. Soc. Chem. Comm., 914, (1977).
Parshall, Ed., *Inorganic Syntheses*, vol. XV, pp. 96–100, McGraw Hill Book Company, Inc., New York, (1974).
Fernelius, Ed., *Inorganic Syntheses*, vol. II, pp. 10–20, McGraw Hill Book Company, Inc., New York, (1946).

*Primary Examiner*—Sam Silverberg
*Attorney, Agent, or Firm*—Donald M. Sell; James A. Smith; Lorraine R. Sherman

[57] ABSTRACT

Preparation of palladium(II) bis(hexafluoroacetylacetonate) and adducts derived therefrom are disclosed, said adducts having the formula $$Pd(F_6ACAC)_2 \cdot L_n$$

wherein L is a Lewis base selected from certain classes, and n is an integer from 1 to 4. These compounds are useful in preparing catalytic and primer surfaces of elemental palladium.

9 Claims, No Drawings

PALLADIUM (II) BIS (HEXAFLUOROACETYLACETONATE), ADDUCTS DERIVED THEREFROM AND USES THEREOF

This is a division of application Ser. No. 351,505, filed Feb. 23, 1982, now U.S. Pat. No. 4,410,569, which is a division of U.S. Ser. No. 159,367, filed June 13, 1980, now U.S. Pat. No. 4,424,352.

TECHNICAL FIELD

This invention relates to palladium(II) bis(hexafluoroacetylacetonate), adducts thereof, and their preparation. In another aspect, it relates to a process for preparing a thin film of active metallic palladium which can be used, for example, as a catalytic surface or as a primer for subsequent physical or chemical reactions. In a further aspect, it relates to a process for catalytically converting CO to $CO_2$, ozone to oxygen, and olefins to alkanes. In still another aspect, it relates to a process for activating surfaces for electroless plating.

BACKGROUND ART

Palladium(II) has been extensively investigated since the late nineteenth century and it has long been recognized that Pd(II) has a coordination number of 4. The coordinated groups, often referred to as ligands, serve as electron donors. Those ligands having two atoms which can simultaneously serve as donors are referred to as bidentate ligands. Chelate ligands, or ring-forming groups, are an important class of bidentate ligands. Such a chelate ligand is the acetylacetonato ion, also referred to as the acetylacetonate anion (often designated as ACAC hereinafter), and may be represented by the structure:

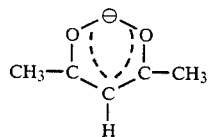

I

The acetylacetonate anion is derived from the enol form of 2,4-pentanedione (a beta-diketone) which exists in equilibrium with its keto form according to the equation:

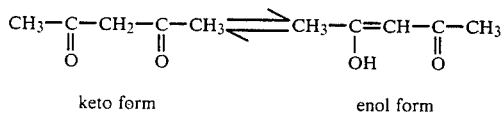

keto form              enol form

Loss of the hydroxy hydrogen of the enol form of 2,4-pentanedione results in the formation of the ACAC anion. Two such ACAC anions coordinate with Pd(II) to form the coordination compound palladium(II) bis-(acetylacetonate):

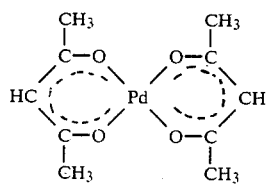

II

The hexafluoroacetylacetonate anion, wherein each $CH_3$ above is replaced by $CF_3$, will be referred to herein as $F_6ACAC$.

General descriptions of the metal complexes of beta-diketones are available: see Fernelius, Ed., *Inorganic Syntheses*, Vol. II, pp. 10–20, McGraw Hill Book Company, Inc., New York (1946) and Sievers and Sadlowski, "Volatile Metal Complexes", Science 201, 217–223 (1978). In these publications, compounds such as aluminum(III) tris(acetylacetonate) and chromium(III) tris-(acetylacetonate) are called metal complexes.

$Pd(ACAC)_2$ and $Pd(F_6ACAC)_2$ have been disclosed in Okeya et al., Chem. Lett., 1305 (1977) and Okeya et al., J. Chem. Soc. Chem. Comm., 914 (1977), but no characterization or physical properties of $Pd(F_6ACAC)_2$ are given.

Metal complexes with fluorinated beta-diketones have been described in Sievers and Sadlowski, supra, although $Pd(F_6ACAC)_2$ is not mentioned.

The two Okeya et al. papers, supra, disclose $Pd(F_6ACAC)_2 \cdot (bipyridine)_2$ and the six tetrakis compounds $Pd(F_6ACAC)_2 \cdot (ammonia)_4$, $Pd(F_6ACAC)_2 \cdot (methylamine)_4$, $Pd(F_6ACAC)_2(ethylamine)_4$, $Pd(F_6ACAC)_2 \cdot (n\text{-propylamine})_4$, $Pd(F_6ACAC)_2 \cdot (ethylenediamine)_2$, and $Pd(F_6ACAC)_2 \cdot (pyridine)_4$. Okeya et al. refer to these compounds as palladium(II) amine complexes.

Bis(hexafluoroacetylacetonate) compounds of nickel-(II) and cobalt(II) are known. See Parshall, Ed., *Inorganic Syntheses*, Vol. XV, pp. 96–100, McGraw Hill Book Company, Inc., New York (1974).

U.S. Pat. No. 3,356,527 discloses vapor plating metals from hexafluoroacetylacetonate compounds of copper, nickel, cobalt, and lead. The patentee suggests that palladium(II) bis(hexafluoroacetylacetonate) appears to have plating potentialities. Such a utility differs from that of the present invention wherein elemental palladium, derived from the palladium(II) bis(hexafluoroacetylacetonate) adducts, is useful as a primer in the electroless plating of other metals. The patentee makes use of 250°–500° C. in the vapor plating process whereas the present invention utilizes temperatures for reduction of the adduct that are below about 150° C.

U.S. Pat. Nos. 3,770,785, 3,876,675 and 3,883,570 disclose bis-chelate derivatives of palladium.

U.S. Pat. No. 3,876,675 discloses fluoroalkyl beta-diketones; however, the compounds described contain two different chelate groups for the palladium atom, one of which may be the hexafluoroacetylacetonate chelate.

U.S. Pat. No. 4,042,603 discloses intramolecular cyclization of substituted diphenylether or benzophenone in the presence of a carboxylic acid salt of palladium and/or palladium organic complexes. $Pd(ACAC)_2$ is listed as a palladium organic complex. Certain components (called promoters) are added with the catalyst in order to increase the yields. Among these are listed acetylacetone and hexafluoroacetylacetone.

U.S. Pat. No. 3,946,057 teaches a process for preparing metal compounds of organic radicals, including $Pd(F_6ACAC)_2$, utilizing a metal halide, a beta-diketone, an alkylene oxide and a polar solvent.

U.S. Pat. No. 3,538,002 discloses the use of beta-diketone metal complexes to reduce oxidation of functional fluids. Palladium bis(hexafluoroacetylacetonate) is included in the specification.

U.S. Pat. No. 3,318,891 discloses complexes of palladium(II) acetate, benzene, pyridine, aniline, benzylamine, quinoline, 2-aminopyrimidine and benzidine.

Although the existence of Pd(F$_6$ACAC)$_2$ is disclosed in the literature, there is no characterization of it or description of its physical properties. However, both Pd(ACAC)$_2$ and Pt(ACAC)$_2$ are reported and characterized.

Although Pd(F$_6$ACAC).L$_n$, wherein L is a Lewis base and n is an integer from 1 to 4, is disclosed in the Okeya et al. papers, supra, for bipyridine (n is 2) and for ammonia, primary amines, and pyridine (n is 4), the preparation of Pd(F$_6$ACAC)$_2$ is not described. Similarly, Pt(F$_6$ACAC)$_2$.(pyridine)$_4$ is disclosed but the preparation of the parent compound is not described.

The prior art refers to compounds having formulas such as Pd(F$_6$ACAC)$_2$.L$_n$ and Pd(F$_6$ACAC)$_2$ as complexes. To avoid misunderstanding, compounds having the formula Pd(F$_6$ACAC)$_2$. L$_n$ will be referred to herein as adducts.

SUMMARY OF THE INVENTION

Briefly, in one aspect of the invention, novel adducts of palladium(II) bis(hexafluoroacetylacetonate) are provided having the formula $$Pd(F_6ACAC)_2.L_n \qquad \qquad III$$

wherein F$_6$ACAC is the hexafluoroacetylacetonate anion, L is a Lewis base selected from certain classes, and n is an integer from 1 to 4, as described in detail hereinafter.

Said adducts and the parent compound, Pd(F$_6$ACAC)$_2$, are useful as catalysts, sources of catalysts, or primers for electroless plating.

The compound Pd(F$_6$ACAC)$_2$ is characterized in Table I.

TABLE I

| | |
|---|---|
| Appearance: | yellow, sublimable crystalline solid |
| M.P. 100° C. | (by differential scanning calorimetry); |
| Heat of fusion: | 10.2 cal/g. |
| Solubility: | 35 g/l hexane at 23° C. |
| | Insoluble in water |

The parent compound Pd(F$_6$ACAC)$_2$ readily sublimes at room temperature in vacuum (10$^{-3}$ torr). The compound will sublime at 80° C. at atmospheric pressure. Although sublimation of fairly large quantities at a slow rate will provide rather large crystals (needles several millimeters in length), the compound can be readily sublimed onto surfaces having certain bases thereon, as will be described hereinafter, to form a very thin film of a Pd(F$_6$ACAC)$_2$ adduct. Such thin films can be utilized, following reduction, to provide a catalytic surface, e.g., to promote oxidation of carbon monoxide to carbon dioxide, or to provide a primer for electroless plating, e.g., copper on palladium primed alumina.

Both Pd(F$_6$ACAC)$_2$ and Pd(F$_6$ACAC)$_2$.L$_n$ can be coated on a surface from solution, but Pd(F$_6$ACAC)$_2$.L$_n$ cannot be coated on a substrate by sublimation.

In contrast to Pd(F$_6$ACAC)$_2$, Pd(F$_6$ACAC)$_2$.L$_n$ adducts are generally non-volatile, less soluble in organic solvents, and decompose directly on heating to form elemental palladium. These adducts are generally less stable and actually decompose at lower temperatures than the parent compound, but this may be advantageous in some cases.

Where the parent compound is sublimed or coated out from solution on certain basic substrates (which are described below), adduct formation takes place and the resulting adducts then can be converted to an elemental palladium coating by heating or chemical reaction, such as by reduction with hydrogen gas, hydrazine, or tetraphenylborate salts. Alternatively, the adducts can be coated from solution and then reduced as described above. Such elemental palladium coatings are then available as catalysts or as primers.

The novel adducts are prepared by reacting Pd(F$_6$ACAC)$_2$ and a Lewis base, as defined below, in a mole ratio appropriate to obtain the desired stoichiometry, i.e., the desired "n" value. Optionally, a solvent may be added such that the reactants are soluble therein. The resulting palladium(II) bis(hexafluoroacetylacetonate) adduct is then recovered. Where a solvent is used, a hydrocarbon such as pentane, hexane, toluene, xylene, benzene, etc., is preferred; but other solvents, such as, alcohols (e.g., methanol, ethanol), ethers, ketones, nitriles, esters, halogenated hydrocarbons (e.g., dichloromethane, chloroform), etc., may also be used. The use of hydrocarbons is particularly advantageous because of their volatility and the low solubility of the adducts in these solvents, making it easy to separate the adducts. The parent compound, palladium(II) bis(hexafluoroacetylacetonate), is prepared from a palladium(II) salt in water by addition of an aqueous basic solution of hexafluoroacetylacetone. The Pd(F$_6$ACAC)$_2$, unhydrated, precipitates and is separated from the solution. The preferred palladium(II) salt is PdCl$_2$, but other palladium(II) salts of mineral acids such as nitric acid and hydrobromic acid can be used. The addition of chloride or bromide ion to the water solution may improve the solubility when palladium(II) halides are used, but this is optional. The chloride or bromide ion may be added as an alkali metal salt or acid, e.g., lithium chloride, sodium chloride, potassium chloride, hydrogen chloride, hydrogen bromide, etc.

A process is disclosed herein for preparing a thin film of catalytically active metallic palladium by reduction of Pd(F$_6$ACAC)$_2$.L$_n$. Such a film provides an improved catalyst system useful, for example, in the conversion of CO to CO$_2$, ozone to oxygen, and olefins to alkanes, such as in the conversion of styrene to ethyl benzene.

Also disclosed herein is a process for using palladium(II) bis(hexafluoroacetylacetonate) and its said Lewis base adducts as primers for activating surfaces for electroless plating.

DETAILED DESCRIPTION OF THE INVENTION

I have found that palladium(II) bis(hexafluoroacetylacetonate) is a stable solid at room temperature and can be readily sublimed. The compound can be easily coated on a substrate by vapor deposition. Alternatively, the compound can be coated onto a substrate from solution. Upon heating the compound after conversion to an adduct in a reducing atmosphere, elemental palladium is obtained. Said Lewis base adducts of the compound can be coated on a substrate from solution and subsequently decomposed to an elemental palladium coating. Unlike the parent compound, said adducts have low vapor pressure and cannot be coated on a substrate by sublimation. Palladium(II) bis(hexafluoroacetylacetonate) adducts can provide a thin film of active metallic palladium which can serve as a catalyst or as a primer for subsequent physical or chemical reactions. As stated above, Pd(F$_6$ACAC)$_2$ can be sublimed onto a basic substrate (e.g., those containing oxides, sulfides, selenides) or ceramics (e.g., substrates comprising barium titanate or niobate, magnesium oxide, etc.) to form an adduct, which may subsequently be decomposed to form an elemental palladium coating. Suitable substrates for coating the adducts include metals such as stainless steel, copper, aluminum, nickel, etc., and refractory substances such as alumina, barium titanate, magnesia, zeolites, cordierite, glass, cermets, etc.

The novel Lewis base adducts of Pd(F$_6$ACAC)$_2$ can be represented as:

$$Pd(F_6ACAC)_2 \cdot L_n \qquad \qquad IV$$

wherein L is a Lewis base selected from certain classes and n is an integer from 1 to 4 depending on the Lewis based used and the desired stoichiometry. Specifically, where n is 1, 2, 3 or 4, L is dimethylethylamine, benzylamine, imidazole, pyrazine, pyrazole, triphenylstibine, benzothiazole, or tert-butylisocyanide; where n is 1, 2 or 3, L is ammonia, methylamine, dimethylamine or pyridine; where n is 1 or 2, L is trimethylamine, triethylphosphine, triphenylphosphine, triphenylarsine, 1,4-dithiane, alumina, silica, or aluminosilicates; where n is 4, L is benzoselenazole; where n is 2, L is 1,2-bis(diphenylphosphino)ethane, phenothiazine, or phenoselenazine; and where n is 1, L is phenazine, trimethylpyridine, bis(2-diphenylphosphinoethyl)-phenylphosphine, phenoxathiin, tetrathianaphthalene, tetrathiatetracene, benzylmethylsulfide, diethylsulfide or bis(diphenylphosphino)acetylene.

The use of elemental palladium as a catalyst is exemplified in the conversion of CO to $CO_2$, ozone to oxygen, or of olefins to alkanes, e.g., styrene to ethylbenzene. The use of the elemental palladium coating as a primer is exemplified in electroless plating of copper or nickel or other metals.

A comparison of Pd(ACAC)$_2$, Pd(F$_3$ACAC)$_2$ and Pd(F$_6$ACAC)$_2$ in electroless plating of copper showed that the latter gave superior results. When a solution of each of these three compounds was coated on alumina and the resulting coated alumina placed in an electroless copper plating bath, all three developed a copper coating on the alumina, but Pd(ACAC)$_2$ caused extensive undesirable plating on the walls of the beaker and there was some plating on the walls of the beaker with Pd(F$_3$ACAC)$_2$, whereas no such extraneous plating was observed on the wall when Pd(F$_6$ACAC)$_2$ was used. These results indicated that an adduct between Pd(F$_6$ACAC)$_2$ and alumina was formed and, although there may have been similar adducts formed between the Pd(ACAC)$_2$ and alumina and Pd(F$_3$ACAC)$_2$ and alumina, the latter two were much less tightly bound.

The adducts formed from Pd(F$_6$ACAC)$_2$ and alumina, silica, or aluminosilicates are not simply a matter of sorption. Alumina and silica are Lewis bases and there is spectroscopic data for concluding that n had the value 1 or 2 for the adducts formed. The formation of the adduct was influenced by the surface activity of these Lewis bases which were characterized by particle size, pore diameter, state of hydration, etc. Two oxygen atoms from the basic material were coordinated to palladium. The oxygen atoms may have come from one molecule or two molecules of base; hence n had the value 1 or 2. The alumina adduct was orange-colored and decomposed on heating at about 130° C. to form palladium metal. The adduct decomposed at a much lower temperature when heated in organic solvents. For example, the adduct decomposed in benzene at 80° C. Solvents useful in reduction of the alumina adducts were aromatic hydrocarbons (e.g., benzene, toluene, etc.), saturated hydrocarbons of 7 or more carbon atoms (e.g., heptane), unsaturated hydrocarbons (e.g., propene, 1-butene, etc.), or alcohols (e.g., methanol, ethanol, cyclohexanol, etc.). The decomposition at such lower temperatures provided more intense catalytic activity due to the fact that increased temperatures tended to decrease the surface area. Hence, preparation of the catalyst at lower temperatures provided more efficient and active catalyst systems. The Pd(F$_6$ACAC)$_2$.alumina complex was reduced by hydrogen at or near room temperature. As used herein alumina means anhydrous Al$_2$O$_3$, boehmite (gamma-AlOOH), diaspore (alpha-AlOOH), gamma-Al$_2$O$_3$, alpha-Al$_2$O$_3$, etc.

The chemistry of Pd(F$_6$ACAC)$_2$ is unexpectedly more diverse than that of previously reported metal acetylacetonates in that Pd(F$_6$ACAC)$_2$.L$_n$ can be prepared in accordance with this invention from a wide variety of certain Lewis bases in a range of stoichiometric ratios (i.e., n may be 1 to 4). In several cases, different values of n for the same ligand were obtained, depending on choice of experimental conditions. For example, Pd(F$_6$ACAC)$_2$.[(CH$_3$)$_2$NH]$_n$ was obtained where n had values of 1, 2 and 4 and these materials were interconvertible (see EXAMPLE 2 below). The availability of such a range of compositions and materials makes the scope and utility of the Pd(F$_6$ACAC)$_2$ adducts very broad compared with other metal hexafluoroacetylacetonates cited in the prior art, supra.

The objects and advantages of this invention are further illustrated by the following examples, but the particular materials and amounts thereof recited in these examples, as well as other conditions and details, should not be construed to unduly limit this invention.

EXAMPLE 1

Preparation of Palladium(II) bis(hexafluoroacetylacetonate)

Palladium(II) chloride, 3.74 g (20 mmole), was dissolved in 8 ml water containing lithium chloride. This solution was filtered into a solution prepared from 8.32 g (40 mmole) hexafluoroacetylacetone and 40 ml 1.0N aqueous sodium hydroxide. After stirring 30 minutes, the solids were collected on a filter, washed with water and dried over calcium chloride.

The crude product was dissolved in 20 ml boiling hexane and filtered. On cooling in a dry ice bath, crystals of Pd(F$_6$ACAC)$_2$ separated and were collected on a filter. Final purification was achieved by sublimation at 70° C. and 70 torr onto a −78° C. probe. The yield was 5.0 g (48% of theory). No impurities were detected by high pressure liquid chromatography. The characterization of this compound was given in detail in Table I, supra. Elemental, spectroscopic, and X-ray crystallographic analyses confirmed the product to be Pd(F$_6$ACAC)$_2$.

EXAMPLE 2

Preparation of Pd(F$_6$ACAC)$_2$.[(CH$_3$)$_2$NH]$_2$, Pd(F$_6$ACAC)$_2$.[(CH$_3$)$_2$NH] and Pd(F$_6$ACAC)$_2$.[(CH$_3$)$_2$NH]$_4$ Dry dimethylamine was passed into a solution of 0.52 g Pd(F$_6$ACAC)$_2$ in 8 ml pentane until yellow crystals began to appear. The reaction mixture was cooled in an ice-salt bath, then filtered to provide 0.58 g of the product as yellow crystals, m.p. 135°–137.5° C. Spectral and elemental analyses confirmed the product to be $Pd(F_6ACAC).[(CH_3)_2NH]_2$.

The filtrate from the above reaction was allowed to evaporate very slowly. The residue contained additional $Pd(F_6ACAC)_2.[(CH_3)_2NH]_2$, and clear orange crystals were obtained of the adduct, $Pd(F_6ACAC)_2.[(CH_3)_2NH]$. Elemental and X-ray crystallographic analyses confirmed the latter product to be $Pd(F_6ACAC)_2.[(CH_3)_2NH]$.

Alternatively, the preparation of $Pd(F_6ACAC)_2.[(CH_3)_2NH]_2$ may be accomplished by removing some of the dimethylamine from $Pd(F_6ACAC)_2.[(CH_3)_2NH]_4$ by applying a vacuum, as described below.

Dry dimethylamine was passed into 0.3 g $Pd(F_6ACAC)_2$ in 8 ml pentane. The yellow crystals which formed initially redissolved and were replaced by white crystals of $Pd(F_6ACAC)_2.[(CH_3)_2NH]_4$ as the introduction of dimethylamine was continued. When the reaction mixture became nearly colorless, it was filtered to yield 0.35 g of the adduct, $Pd(F_6ACAC)_2.[(CH_3)_2NH]_4$, m.p. 179° C. (dec.), confirmed by spectroscopic and elemental analyses. A sample of $Pd(F_6ACAC)_2.[(CH_3)_2NH]_4$ was maintained under dynamic vacuum (ca. $3 \times 10^{-3}$ torr) for several hours, during which time the crystals turned yellow. The X-ray powder diffraction pattern of the product obtained matched that of $Pd(F_6ACAC)_2.[(CH_3)_2NH]_2$ described above.

EXAMPLE 3

Preparation of $Pd(F_6ACAC)_2.(phenazine)$ $Pd(F_6ACAC)_2$, 1.0 mmole (0.52 g), in 2 ml toluene and 1.0 mmole phenazine (0.18 g) in 8 ml hot toluene were combined. On cooling in an ice bath, yellow crystalline flakes separated and they were collected on a filter. This crude product was heated at 50° C./$2 \times 10^{-3}$ torr in a sublimer fitted with a dry ice cooled probe. The residue weighed 0.2 g and was the adduct, $Pd(F_6ACAC)_2.(phenazine)$, confirmed by spectroscopic and elemental analyses.

EXAMPLE 4

Preparation of $Pd(F_6ACAC)_2.(phenoxathiin)$ $Pd(F_6ACAC)_2$, 0.5 mmole (0.26 g) and 1.0 mmole (0.20 g) phenoxathiin were combined in 6 ml hexane. The orange solution was cooled to $-78°$ C. The solids which separated were collected on a filter and then heated (warm water bath) in a vacuum sublimer fitted with a dry ice cooled probe. The nonvolatile residue constituted the adduct, $Pd(F_6ACAC)_2.(phenoxathiin)$, 0.20 g, m.p. 92°–93° C., as confirmed by spectroscopic and elemental analyses.

EXAMPLE 5

Preparation of $Pd(F_6ACAC)_2.[2,6-(CH_3)_2C_5H_3N]$ $Pd(F_6ACAC)_2$ (0.2 g) in 8 ml pentane as treated with excess 2,6-dimethylpyridine. Briefly cooling the orange solution in a dry ice bath yielded 0.19 g of solid product. Recrystallization from hexane afforded yellow needles, m.p. 131°–132° C. Spectroscopic and elemental analyses confirmed the product to be $Pd(F_6ACAC)_2.[2,6-(CH_3)_2C_5H_3N]$.

EXAMPLE 6

Preparation of $Pd(F_6ACAC)_2.[(C_6H_5)_3As]_2$

A solution of 1.1 mmole (0.33 g) $(C_6H_5)_3As$ in 10 ml warm hexane was added with stirring to 0.5 mmole (0.26 g) $Pd(F_6ACAC)_2$ in 3 ml of the same solvent. The solids which separated were recrystallized from dichlormethanehexane to give 0.45 g of $Pd(F_6ACAC)_2.[(C_6H_5)_3As]_2$ as dark red needles, m.p. 132°–133° C., as confirmed by spectroscopic and elemental analyses.

EXAMPLE 7

Preparation of $Pd(F_6ACAC)_2.(Phenoselenazine)_2$

Commercial phenoselenazine was purified by recrystallization from toluene, followed by vacuum sublimation. Pure phenoselenazine (0.32 g, 1.3 mmole) and 0.34 g (0.66 mmole) $Pd(F_6ACAC)_2$ were combined in 3 ml each acetone and benzene. The acetone was removed under reduced pressure. The product separated as a deep blue powder which was filtered and washed with pentane, yield 0.53 g. Spectroscopic and elemental analyses confirmed the product to be $Pd(F_6ACAC)_2.(phenoselenazine)_2$.

EXAMPLES 8–23

The following adducts were prepared using the general method of EXAMPLE 2. Elemental and spectroscopic analyses of the compounds confirmed their structure.

TABLE II

| Example | Compound |
| --- | --- |
| 8 | $Pd(F_6ACAC)_2.[(C_6H_5)_3Sb]_4$ |
| 9 | $Pd(F_6ACAC)_2.(1,4-C_4H_8S_2)_2$ |
| 10 | $Pd(F_6ACAC)_2.(phenothiazine)_2$ |
| 11 | $Pd(F_6ACAC)_2.(phenazine)$ |
| 12 | $Pd(F_6ACAC)_2.(benzothiazole)_4$ |
| 13 | $Pd(F_6ACAC)_2.[(CH_3)_3N]_2$ |
| 14 | $Pd(F_6ACAC)_2.[2,6(CH_3)_2C_5H_3N]$ |
| 15 | $Pd(F_6ACAC)_2.(1,2-[(C_6H_5)_2P]_2C_2H_4)_2$ |
| 16 | $Pd(F_6ACAC)_2.(phenoxathiin)$ |
| 17 | $Pd(F_6ACAC)_2.[2,4,6-(CH_3)_3C_5H_2N]$ |
| 18 | $Pd(F_6ACAC)_2.[(C_6H_5)_2PC_2H_4]_2PC_6H_5$ |
| 19 | $Pd(F_6ACAC)_2.(tert-C_4H_9NC)_2$ |
| 20 | $Pd(F_6ACAC)_2.(tert-C_4H_9NC)_4$ |
| 21 | $Pd(F_6ACAC)_2.[(C_6H_5CH_2)(CH_3)S]$ |
| 22 | $Pd(F_6ACAC)_2.[(C_6H_5)_2PC_2P(C_6H_5)_2]$ |
| 23 | $Pd(F_6ACAC)_2.(SiO_2)_{1 \text{ or } 2}$ |

EXAMPLE 24

Preparation of Palladium(II) bis(hexafluoroacetylacetonate).alumina and its Hydrogen Reduction to Elemental Palladium Catalyst Alumina granules, 15 g, and 0.75 g powdered $Pd(F_6ACAC)_2$ were placed in a flask. This was attached to a vacuum line and evacuated to $5 \times 10^{-3}$ torr and sealed. The flask was shaken from time to time for six hours during which the alumina turned orange due to the formation of an adduct. Granules (5.0 g) were placed in a glass tube between two plugs of glass wool. The apparatus was thoroughly flushed with nitrogen and placed in a 100° C. oil bath. Hydrogen was slowly passed over the granules for three hours. During this time, the granules slowly darkened and finally became black. The catalyst so produced (surface area, 108 m$^2$g-1) was tested by the conversion of CO to $CO_2$ (90% conversion in air, at 50 ppm CO feed).

EXAMPLE 25

Propylene Reduction of Palladium(II) bis(hexafluoroacetlyacetonate).alumina to Elemental Palladium Pd(F$_6$ACAC)$_2$.alumina (1% Pd by weight) having a total weight of 0.2 g, was placed in a U-tube. Propylene was passed over the solid at room temperature but very little evidence of reaction was observed. The tube was placed in a 75° C. oil bath. The solids rapidly darkened and turned black, thus indicating that reduction had taken place.

EXAMPLE 26

Preparation of Elemental Palladium on Alumina from Pd(F$_6$ACAC)$_2$.alumina, Catalyst for Conversion of (a) Styrene to Ethylbenzene and (b) 1-Octene to Octane (a) The utilization of Pd(F$_6$ACAC)$_2$.alumina as a catalyst source was demonstrated by the following reaction. A mixture of 3.0 g alumina, 0.3 g Pd(F$_6$ACAC)$_2$ and 20 ml benzene (solvent and reducing agent) was stirred and refluxed for 24 hours, during which time the orange color in the benzene phase was discharged. The suspension was filtered hot, and the solids washed with benzene and air dried. The surface area of the product was 119 m$^2$g$^{-1}$. No palladium metal was observed on the glass apparatus.

Five grams of styrene, 55 ml of ethanol and 1.0 g of the above product were treated with hydrogen at 55° C. and 5170 torr. The reactor was repressured from time to time to maintain, approximately, 5170 torr. After the uptake of hydrogen ceased, the pressure drop corresponded to an 89% reduction of the olefinic double bond. Gas chromatographic analysis of the reaction mixture revealed that the ratio of ethylbenzene to styrene was 199:1.

(b) Following the same procedure, 1-octene was converted to octane.

EXAMPLE 27

Preparation of Elemental Palladium on Alumina from Pd(F$_6$ACAC)$_2$.alumina, Catalyst for Oxidation of CO to CO$_2$ Fifty grams of alumina granules, shown by X-ray diffraction analysis to be mostly gamma-AlOOH with some alpha-Al(OH)$_3$ and possibly some gamma-Al$_2$O$_3$, 2.5 g Pd(F$_6$ACAC)$_2$ and 250 ml benzene (solvent and reducing agent) were placed in a 250 ml flask fitted with a paddle stirrer and reflux condenser. The stirrer was operated only intermittently to prevent self-abrasion of the granules. After about 20 minutes at reflux temperature, the yellow solution became colorless and the granules became dark gray to black due to reduction. The granules were collected on a filter, washed with pentane, and dried in air. The granules contained 1% Pd by weight. No hexafluoroacetylacetone could be detected in the benzene phase by infrared or gas chromatographic analysis.

Examination of the catalyst granules by scanning electron microscopy revealed the presence of palladium but no metal crystallites were seen at 3000X magnification. Light microscopy disclosed that the metal was localized in a 3-6 micron thick region on the outside of the granules.

The catalyst (10 g) was tested for activity by oxidation of CO to CO$_2$. A solution of 50 ppm CO in air was employed, and percentage conversion measured by infrared analysis. The surface of the supported catalyst was 218 m$^2$/g and the conversion of CO to CO$_2$ was 100%.

EXAMPLE 28

Preparation of Elemental Pd Catalyst from Pd(F$_6$ACAC)$_2$ for Ozone Decomposition A corrugated ceramic monolith which was determined to be mostly cordierite by X-ray diffraction analysis was submerged in a solution of 1.0 g Pd(F$_6$ACAC)$_2$ in 100 ml benzene (solvent and reducing agent) and refluxed for 16 hours, after which it was removed, washed by immersion in benzene and air dried. On evaporation of the benzene solutions, 0.74 g Pd(F$_6$ACAC)$_2$ was recovered. The mass balance indicated that the monolith contained 0.24% Pd by weight as palladium metal indicating that not all of the palladium(II) bis(hexafluoroacetylacetonate) had been consumed.

Two additional cores were prepared separately by immersing them in water solutions of PtCl$_6^{2-}$ and PdCl$_4^{2-}$, followed by drying and firing for two hours in air at 288° C. All three catalysts were tested for activity in ozone decomposition. The conditions were: air flow rate of 4.33×10$^5$ cm$^3$/min; pressure of 3.6 torr; contact time of 5.3×10$^{-3}$ sec; concentration of O$_3$ entering the test reactor was 3 ppm; temperature of 177° C. Results are shown below:

TABLE III

| Catalyst | % O$_3$ decomposed |
|---|---|
| 0.90% Pt (aqueous impregnation) | 85 |
| 0.24% Pd [from Pd(F$_6$ACAC)$_2$] | 71 |
| 0.64% Pd (aqueous impregnation) | 79 |

The results indicated that fairly comparable catalytic activity was achieved with much less Pd loading when Pd(F$_6$ACAC)$_2$ was used.

EXAMPLE 29

Primer for Electroless Plating

Granules coated with 0.2% Pd were prepared from Pd(F$_6$ACAC)$_2$.alumina, using the procedure of EXAMPLE 27. They were added to an electroless copper plating bath (see U.S. Pat. No. 3,595,684, column 7 for composition of plating bath) at room temperature and were removed therefrom after five minutes. Visual and light microscopic examination revealed that they were coated with a coppery deposit. Alumina granules not so treated are not plated.

EXAMPLE 30

Primer for Electroless Plating

Alumina granules were coated with Pd(F$_6$ACAC)$_2$.alumina by immersion under ambient conditions in a heptane solution containing Pd(F$_6$ACAC)$_2$. The resulting orange colored granules were separated by filtration and were treated with an electroless copper plating bath as described in Example 29. The granules quickly became dark and gas bubbles arose from them. On removal from the plating bath, the granules were seen to be covered with a copper film. Several granules were firmly pressed between two layers of Scotch brand Magic Transparent tape. When the two layers were peeled apart, the copper coat did not separate from the alumina granules.

EXAMPLE 31

Primer for Electroless Plating (solvent-free)

Alumina granules, 2.0 g, and 0.1 g Pd(F$_6$ACAC)$_2$ were placed in a flask and evacuated to a nominal pressure of 3.5 torr. After about five minutes the granules had taken on a orange color which was due to the formation of the adduct. The granules were plated with copper as described in Example 29.

EXAMPLES 32-34

Primers for Electroless Plating Using Different Palladium Chelates

Palladium chelates were coated onto separate samples of alumina powder from benzene solution. The alumina samples were then placed in an electroless copper plating bath and the relative effects of the different chelates estimated visually. All three samples of palladium activated alumina were plated with copper but dramatic differences were noted and are indicated below. In all cases copper plated on the alumina granules. Additional data is given below.

TABLE IV

| Example | Pd chelate | Result |
|---------|------------|--------|
| 32 | Pd(ACAC)$_2$ | Extensive plating on vessel walls |
| 33 | Pd(F$_3$ACAC)$_2$ | Some plating on vessel walls |
| 34 | Pd(F$_6$ACAC)$_2$ | No plating on vessel walls |

Various modifications and alterations of this invention will become apparent to those skilled in the art without departing from the scope and spirit of this invention, and it should be understood that this invention is not to be unduly limited to the illustrative embodiments set forth herein.

I claim:

1. A method comprising the steps:
   (1) coating a solution of an adduct of palladium(II) bis(hexafluoroacetylacetonate) onto a basic substrate, said adduct of palladium(II) bis(hexafluoroacetylacetonate) having the formula Pd(F$_6$ACAC)$_2$·L$_n$ wherein
   F$_6$ACAC is the hexafluoroacetylacetonate anion,
   L is a Lewis base and n is an integer 1 to 4, with the provisos that
   when n is 1, 2, 3 or 4, L is dimethylethylamine, benzylamine, imidazole, pyrazine, pyrazole, triphenylstibine, benzothiazole, or tert-butylisocyanide,
   when n is 1, 2, or 3, L is ammonia, methylamine, dimethylamine, or pyridine,
   when n is 1 or 2, L is trimethylamine, triphenylphosphine, triphenylarsine, 1,4-dithiane, alumina, silica, or aluminosilicates,
   when n is 4, L is benzoselenazole,
   when n is 2, L is 1,2-bis(diphenylphosphino)ethane, phenothiazine, or phenoselenazine,
   when n is 1, L is phenazine, trimethylpyridine, bis(2-diphenylphosphinoethyl)phenylphosphine, phenoxathiin, tetrathianaphthalene, tetrathiatetracene, benzylmethylsulfide, diethylsulfide, or bis(diphenylphosphino)acetylene,
   (2) evaporating the solvent from the resulting coating, and
   (3) reducing the resulting solvent-free coating to provide a catalytically active surface of palladium.

2. A method according to claim 1 wherein said substrate is selected from metals and refractory substances.

3. The method according to claim 1 further comprising passing carbon monoxide gas over said catalytically active surface of palladium in the presence of air to produce carbon dioxide gas.

4. The method according to claim 1 further comprising reacting an olefin with hydrogen gas in the presence of said catalytically active surface of palladium to produce an alkane.

5. The method according to claim 1 further comprising passing ozone over said catalytically active surface of palladium to produce oxygen.

6. A method according to claim 1 wherein said step of reducing takes place in the presence of a compound selected from the class consisting of hydrazine, sodium tetraphenylborate, hydrogen gas, benzene, and propylene.

7. A method for making a primer for electroless plating of metals, said method comprising the steps according to claim 1, and then subjecting the resulting reduced material to an electroless metal plating bath.

8. A method according to claim 7 wherein said step of reducing takes place in the presence of a compound selected from the class consisting of hydrazine, sodium tetraphenylborate, hydrogen gas, benzene, and propylene.

9. The method according to claim 7 wherein said reducing step is accomplished by including a reducing compound in said electroless metal plating bath.

* * * * *